US008586561B2

(12) United States Patent
Kazuno

(10) Patent No.: US 8,586,561 B2
(45) Date of Patent: Nov. 19, 2013

(54) ANTI-TUMOR AGENT COMPRISING CYTIDINE DERIVATIVE AND CARBOPLATIN

(75) Inventor: Hiromi Kazuno, Hanno (JP)

(73) Assignees: Taiho Pharmaceutical Co., Ltd., Tokyo (JP); Takuma Sasaki, Nagoya-shi (JP); Akira Matsuda, Sapporo-shi (JP)

( * ) Notice: Subject to any disclaimer, the term of this patent is extended or adjusted under 35 U.S.C. 154(b) by 205 days.

(21) Appl. No.: 12/934,772

(22) PCT Filed: Mar. 26, 2009

(86) PCT No.: PCT/JP2009/001351
§ 371 (c)(1),
(2), (4) Date: Dec. 27, 2010

(87) PCT Pub. No.: WO2009/119092
PCT Pub. Date: Oct. 1, 2009

(65) Prior Publication Data
US 2011/0118205 A1 May 19, 2011

(30) Foreign Application Priority Data

Mar. 27, 2008 (JP) ................................ 2008-082690

(51) Int. Cl.
*A01N 43/04* (2006.01)
*A61K 31/70* (2006.01)

(52) U.S. Cl.
USPC .......................................................... 514/49

(58) Field of Classification Search
None
See application file for complete search history.

(56) References Cited

U.S. PATENT DOCUMENTS

| | | | |
|---|---|---|---|
| 5,763,418 | A | 6/1998 | Matsuda et al. |
| RE38,090 | E | 4/2003 | Matsuda et al. |
| 6,544,962 | B1 * | 4/2003 | Jones et al. ........... 514/49 |
| 2010/0120709 | A1 | 5/2010 | Kazuno et al. |

FOREIGN PATENT DOCUMENTS

| | | |
|---|---|---|
| EP | 2 145 625 A1 | 1/2010 |
| JP | 3142874 | 12/2000 |
| JP | 2007 277240 | 10/2007 |

OTHER PUBLICATIONS

Alberts et al. The Oncologist 1998; 3:15-34.*
Hattori et al. J. Med. Chem. 1996, 39, 5005-5011.*
European Search Report issued Dec. 5, 2011, in Patent Application No. 09726269.5.
Hiromi Kazuno, et al., "1-(3-*C*-Ethynyl-β-D-*ribo*-pentofuranosyl)cytosine(ECyd,TAS-106), a novel potent inhibitor of RNA polymerase, potentiates the cytotoxicity of CDDP in human cancer cells both in vitro and in vivo", International Journal of Oncology, vol. 34, No. 5, XP002605648, Jan. 1, 2009, pp. 1373-1380.
Kazuno, Hiromi et al., "Combination effect of TAS106 (3'-C-ethynylcytidine, Ecyd) with various anticancer drugs in vitro:", The Japanese Cancer Association, pp. 558, col. 1933, (Aug. 25, 2001), (with English translation).
Motohiro, Tanaka et al., "Enhancement of antitumor activity of 3'-ethynilcytidine (Ecyd) with CDDP:", Japanese Cancer Association, p. 710, col. 2395, (Aug. 30, 1999), (with English translation).
Wataya, Yusuke et al., Anticancer molecular mechanism of 3'-ethynylcytidine (ECyd), Nucleic Acids Research Supplement, No. 1, pp. 233-234, (2001).
International Search Report issued May 12, 2009 in PCT/JP09/01351 filed Mar. 26, 2009.
Written Opinion issued May 12, 2009 in PCT/JP09/01351 filed Mar. 26, 2009.
Makoto Ogawa, et al., "The Current Status of Clinical Research of New Anticancer Drug", Igaku no Ayumi (Advances in Medicine), 1978, vol. 141, No. 9, pp. 550-553.
Keiichi Fujiwara, et al., "Anticancer Drug: Platinum Derivative", Medicine and Drug Journal, 1994, vol. 30, Extra Number, pp. 169-172.
Masakazu Yokoyama, "Platinum-Containing Drug", Antibiotics & Chemotherapy, 1987, vol. 3, No. 11, pp. 1839-1849.
Ian Judson, "New Developments and Approaches in the Platinum Arena", Drugs, 2000, vol. 59, Supplement 4, pp. 29-36.
Office Action issued on Jun. 25, 2013 for Japanese Patent Application No. 2010-505353 (with English translation).
Examination Report Issued Aug. 28, 2013 in Australian Patent Application No. 2009230499.
Satoshi Tabata et al., "Antitomor effect of anovel multifuncioanl antitumor nucleoise, 3'-ethynulcytidine, on human cancers", Oncology Reports, vol. 3, pp. 1029-1034, 1996.

* cited by examiner

*Primary Examiner* — Layla Bland
(74) *Attorney, Agent, or Firm* — Oblon, Spivak, McClelland, Maier & Neustadt, L.L.P.

(57) ABSTRACT

Provision of a novel combined therapy with ECyd, which therapy exhibits remarkable antitumor effect and gives less adverse effects.
The invention provides an antitumor agent containing, in combination, 1-(3-C-ethynyl-β-D-ribopentofuranosyl)cytosine or a salt thereof and carboplatin.

12 Claims, 2 Drawing Sheets

ANTI-TUMOR AGENT COMPRISING CYTIDINE DERIVATIVE AND CARBOPLATIN

TECHNICAL FIELD

The present invention relates to an antitumor agent containing a cytidine derivative and carboplatin in combination and to an agent for potentiating the antitumor effect of carboplatin.

BACKGROUND ART 1-(3-C-Ethynyl-β-D-ribopentofuranosyl)cytosine (ECyd, represented by the following formula) is an antimetabolite having a structure in which the 3'-β-position of the ribose of cytidine is substituted by an ethynyl group.

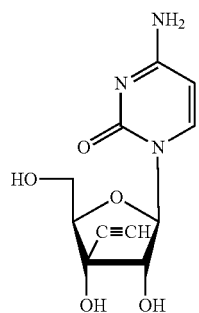

[F1]

ECyd is a cytidine derivative which was first synthesized in Japan. Differing from a pyrimidine derivative (5-FU) or a deoxycytidine derivative (gemcitabine), which are antitumor agents generally employed in the clinical settings, ECyd weakly acts on DNA and mainly inhibits RNA synthesis. Specifically, in a proposed mechanism, ECyd is phosphorylated by intracellular uridine/cytidine kinase, to thereby form a triphosphate (ECTP), which inhibits RNA polymerases I, II, and III, leading relevant cells to death (Patent Document 1 and Non-Patent Document 1).

Many antitumor agents which are generally employed in the clinical settings and which work based on DNA synthesis inhibition as a main action exhibit the inhibitory effect in an S-phase. Tumor cells employed in animal tests generally exhibit relatively fast proliferation. However, studies have revealed that, in the clinical settings, tumor cells proliferate at a slow rate, and a small number of the cells are in the S-phase. Since, differing from DNA synthesis inhibiting agents, the antitumor effect of ECyd based on RNA synthesis inhibitory action is not affected by the cell cycle of tumor cells, ECyd is thought to serve as a clinically useful antitumor agent, which differs from DNA synthesis inhibiting agents generally employed in the clinical settings.

Another attempt has been made to further potentiate the antitumor effect of ECyd, in which an antitumor agent such as cisplatin, having a different action mechanism, is employed in combination (Non-Patent Document 2). However, hitherto, a satisfactory potentiating effect has not been attained. Therefore, there is keen demand for a new combined therapy with ECyd, which therapy exhibits a more potent antitumor effect and gives less adverse effects.

RELATED ART DOCUMENTS

Patent Document 1: Japanese Patent No. 3142874
Non-Patent Document 1: Nucleic Acids Res. Suppl. 1, 233-4, (2001)
Non-Patent Document 2: Proceedings of the Annual Meeting of the Japanese Cancer Association 60, 558, (2001)

DISCLOSURE OF THE INVENTION

Problems to be Solved by the Invention

The present invention is directed to provision of a novel combined therapy with ECyd, which therapy exhibits remarkable antitumor effect and gives less adverse effects.

Means for Solving the Problems

In view of the foregoing, the present inventor has carried out extensive studies on a novel combined therapy employing Ecyd and another antitumor agent in combination for providing a cancer therapy enabling patients to survive for a longer period of time, and has found that an antitumor effect can be remarkably potentiated without increasing adverse effects, through employment, in combination, of ECyd and a platinum complex cis-diammine(1,1-cyclobutanedicarboxylato)platinum(II) (nonproprietary name: carboplatin, hereinafter abbreviated as CBDCA). The inventor has also found that the thus-obtained antitumor effect is more effective than the antitumor effect of a similar combined therapy employing cisplatin, which has a chemical structure and an action mechanism similar to those of CBDCA.

Accordingly, the present invention is directed to the following 1) to 8).

1) An antitumor agent containing, in combination, 1-(3-C-ethynyl-β-D-ribopentofuranosyl)cytosine or a salt thereof, and carboplatin.

2) An antitumor agent according to 1) above, which is a combined drug.

3) An antitumor agent according to 1) above, which is in the form of a kit including a drug containing 1-(3-C-ethynyl-β-D-ribopentofuranosyl)cytosine or a salt thereof and a drug containing carboplatin.

4) An agent for potentiating the antitumor effect of carboplatin, which agent contains 1-(3-C-ethynyl-β-D-ribopentofuranosyl)cytosine or a salt thereof in such an amount that the antitumor effect of carboplatin is significantly potentiated.

5) Use, for producing an antitumor agent, of 1-(3-C-ethynyl-β-D-ribopentofuranosyl)cytosine or a salt thereof and carboplatin in combination.

6) A method for treating cancer, comprising administering, in combination, 1-(3-C-ethynyl-β-D-ribopentofuranosyl)cytosine or a salt thereof and carboplatin, to a patient in need thereof.

7) A method for treating cancer according to 6) above, wherein 1-(3-C-ethynyl-β-D-ribopentofuranosyl)cytosine or a salt thereof and carboplatin are administered to a patient in need thereof simultaneously, or separately at an interval.

8) A method for potentiating the antitumor effect of carboplatin, comprising administering, to a patient to which carboplatin is administered, 1-(3-C-ethynyl-β-D-ribopentofuranosyl)cytosine or a salt thereof in such an amount that the antitumor effect of carboplatin is significantly potentiated.

Effects of the Invention

According to the antitumor agent of the present invention, a cancer therapy exhibiting high antitumor effect can be performed while suppressing adverse effects, whereby the survival of patients can be prolonged.

BEST MODES FOR CARRYING OUT THE INVENTION

Figure 1:
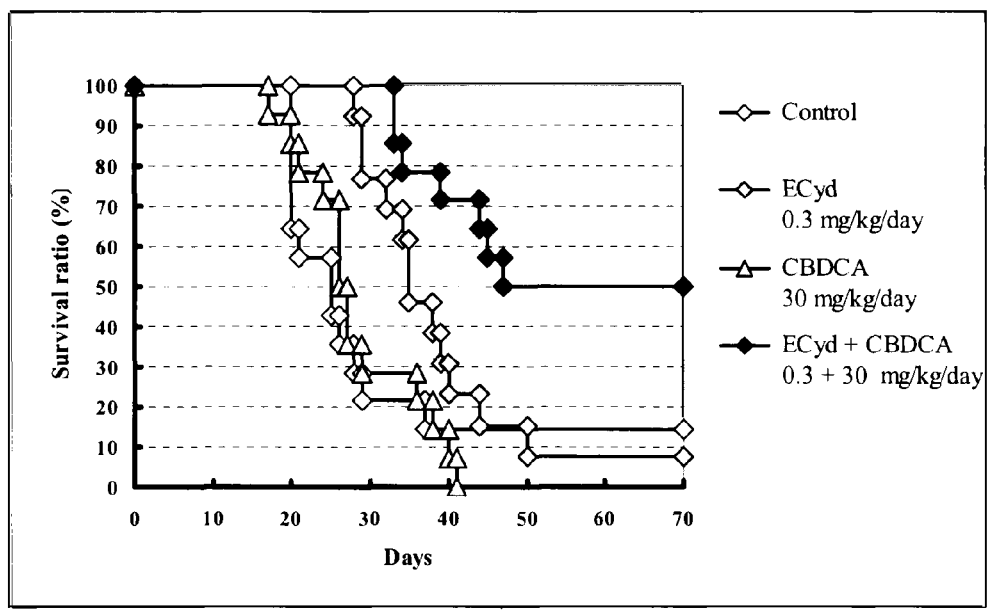
FIG. 1 A graph showing survival of subjects to which 0.3 mg/kg/day ECyd and 30 mg/kg/day carboplatin have been administered in combination.

ECyd, 1-(3-C-ethynyl-β-D-ribopentofuranosyl)cytosine, employed in the present invention is a known compound and is known to exhibit an antitumor effect to a variety of cancers through RNA synthesis inhibitory action. Notably, there has never been reported that cancer can be effectively treated with suppressing adverse effects through employment of ECyd and CBDCA.

No particular limitation is imposed on the salt of ECyd, so long as it is pharmaceutically acceptable. Examples of the salt include inorganic acid salts such as hydrochlorides, hydrobromides, sulfates, nitrates, and phosphates; and organic acid salts such as acetates, propionates, tartrates, fumarates, maleates, malates, citrates, methanesulfonates, p-toluenesulfonates, and trifluoroacetates.

ECyd or a salt thereof may be produced through a known method, for example, a method disclosed in Japanese Patent No. 3142874.

CBDCA, cis-diammin(1,1-cyclobutanedicarboxylato)platinum(II), employed in the present invention is a known platinum complex and is known to exhibit an antitumor effect through DNA synthesis inhibitory action. CBDCA may be produced through a known method, for example, a method disclosed in JP-B-1981-029676. Also, a commercial drug, for example, Paraplatin (registered trademark, Bristol Meyers), may be employed.

As described in the Examples hereinbelow, through employment in combination of ECyd or a salt thereof and CBDCA, a remarkably strong antitumor effect can be attained as compared with administration of either of the component singly. Therefore, a pharmaceutical product containing ECyd or a salt thereof and CBDCA as effective ingredients is a useful antitumor agent. Furthermore, a pharmaceutical product containing ECyd or a salt thereof as an effective ingredient is a useful agent for potentiating the antitumor effect of CBDCA, and a pharmaceutical product containing CBDCA as an effective ingredient is a useful agent for potentiating the antitumor effect of ECyd or a salt thereof.

No particular limitation is imposed on the cancer which can be treated by the antitumor agent of the present invention. Examples of the cancer include head and neck cancer, esophageal cancer, stomach cancer, colon cancer, rectal cancer, liver cancer, gallbladder/bile duct cancer, pancreatic cancer, lung cancer, breast cancer, ovarian cancer, bladder cancer, prostate cancer, testicular tumor, bone and soft tissue sarcoma, malignant lymphoma, leukemia, cervical cancer, skin cancer, and brain tumor. The cancer is preferably head and neck cancer or lung cancer.

The form of the antitumor agent of the present invention may be a combined drug in which the aforementioned ECyd or a salt thereof and CBDCA are mixed at an appropriate ratio, each at an effective amount, to form a single dosage form (single-formulation type), or a pharmaceutical product including the drugs in effective amounts separately for enabling the aforementioned ingredients to be administered simultaneously, or separately at an interval (double-formulation type).

No particular limitation is imposed on the administration form of the aforementioned pharmaceutical product, and an appropriate form may be selected in accordance with the therapeutic purpose. Examples of the form of the pharmaceutical product include oral agents (e.g., tablets, coated tablets, powder, granules, capsules, and liquid), injections, suppositories, cataplasms, and ointments. ECyd or a salt thereof and CBDCA may be administered in the forms identical to or different from each other.

The pharmaceutical products employed in the present invention and containing ECyd or a salt thereof and/or CBDCA may be prepared through a generally known method by use of a pharmacologically acceptable carrier. Such a carrier may be selected from a variety of carriers generally employed in drugs. Specific examples include a excipient, a binder, a disintegrant, a lubricant, a diluent, a solubilizing agent, a suspending agent, a tonicity agent, a pH-adjusting agent, a buffer, a stabilizer, a coloring agent, a flavoring agent, and a deodorant.

Examples of the excipient include lactose, sucrose, sodium chloride, glucose, maltose, mannitol, erythritol, xylitol, maltitol, inositol, dextran, sorbitol, albumin, urea, starch, calcium carbonate, kaolin, crystalline cellulose, silicic acid, methylcellulose, glycerin, sodium alginate, gum arabic, and mixtures thereof. Examples of the lubricant include purified talc, stearate salts, borax, polyethylene glycol, and mixtures thereof. Examples of the binder include simple syrup, glucose liquid, starch liquid, gelatin solution, polyvinyl alcohol, polyvinyl ether, polyvinylpyrrolidone, carboxymethylcellulose, shellac, methylcellulose, ethylcellulose, water, ethanol, potassium phosphate, and mixtures thereof. Examples of the disintegrant include dry starch, sodium alginate, powdered agar, powdered laminaran, sodium hydrogencarbonate, calcium carbonate, polyoxyethylene sorbitan fatty acid esters, sodium lauryl sulfate, stearic monoglyceride, starch, lactose, and mixtures thereof. Examples of the diluent include water, ethyl alcohol, Macrogol, propylene glycol, ethoxylated isostearyl alcohol, polyoxylated isostearyl alcohol, polyoxyethylene sorbitan fatty acid esters, and mixtures thereof. Examples of the stabilizer include sodium pyrosulfite, ethylenediaminetetraacetic acid, thioglycolic acid, thiolactic acid, and mixtures thereof. Examples of the tonicity agent include sodium chloride, boric acid, glucose, glycerin, and mixtures thereof. Examples of the pH-adjusting agent and buffer include sodium citrate, citric acid, sodium acetate, sodium phosphate, and mixtures thereof. Examples of soothing agents include procaine hydrochloride, lidocaine hydrochloride, and mixtures thereof.

Generally, the pharmaceutical product preferably contains ECyd or a salt thereof and CBDCA in amounts of 0.1 to 100 mg and 0.01 to 10 g, respectively.

When the antitumor agent of the present invention is provided as a kit, the kit may be designed to include separate packages of a drug containing ECyd or a salt thereof as prepared above and a drug containing CBDCA, so that the drugs are separately taken from the corresponding packages before use. Alternatively, each pharmaceutical formulation may be held in one package suitable for use at each event of combined administration.

In the present invention, no particular limitation is imposed on the amount of ECyd or a salt thereof and that of CBDCA administered to a patient, so long as ECyd or a salt thereof and CBDCA synergistically exhibit antitumor effect to treat cancer, and the amounts are appropriately predetermined in accordance with the age, type of cancer, stage of cancer, presence of metastasis, or therapy history of a patient, presence of other antitumor agents, etc. Typically, the amount of ECyd or a salt thereof (as reduced to ECyd) is about 0.01 to 200 mg/m$^2$/day, and the amount of CBDCA is 0.01 to 20 g/m$^2$/day. Preferably, the amount of ECyd or a salt thereof (as reduced to ECyd) is about 0.05 to 100 mg/m$^2$/day, and the amount of CBDCA is 0.1 to 10 g/m$^2$/day.

In the present invention, no particular limitation is imposed on the sequence and intervals of administration of ECyd or a salt thereof and CBDCA, so long as a target synergistic effect can be attained. When the kit is used, separated drug ingredients may be administered simultaneously or intermittently.

EXAMPLES

Example 1

Male nude rats (F344/N Jcl-rnu) were divided in terms of body weight into groups (14 rats in each group). To each rat, a fragment (about 2×2 mm) of human head and neck cancer strain OCC-1 was subcutaneously transplanted into the back (day 0). Drug administration was started on the day following transplant (day 1). ECyd was administered to a rat through the caudal vein at a dose of 0.3 mg/kg on days 1, 3, 5, 8, 10, and 12. Carboplatin was administered to a rat through the caudal vein at a dose of 30 mg/kg or 40 mg/kg on days 1 and 8. Cisplatin was administered to a rat through the caudal vein at a dose of 5 mg/kg on day 1. Note that carboplatin (40 mg/kg/day) and cisplatin (5 mg/kg/day) employed in the test exhibited almost the same antitumor effect. Rats of a control group were not subjected to drug treatment.

Figure 2:
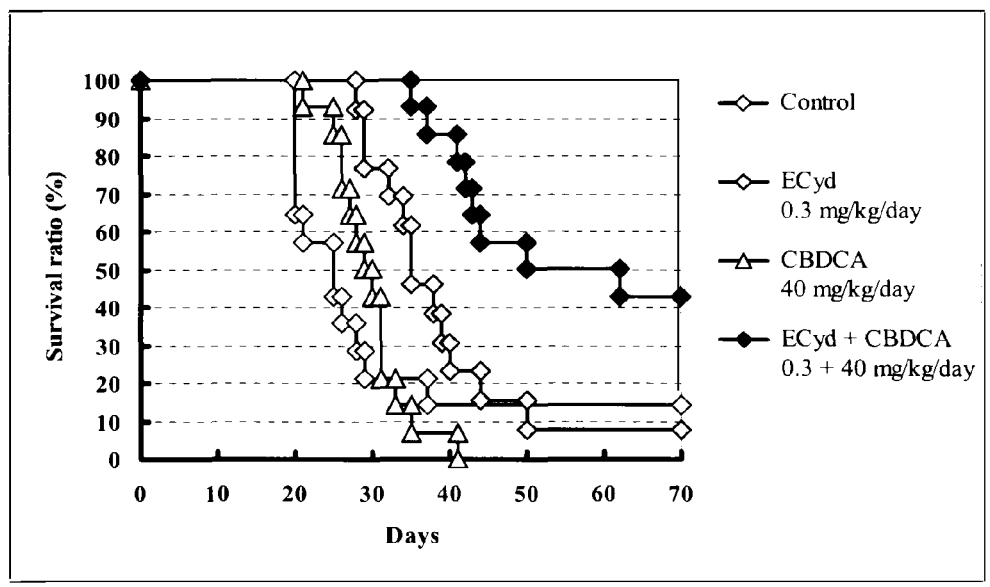
FIG. 2 A graph showing survival of subjects to which 0.3 mg/kg/day ECyd and 40 mg/kg/day carboplatin have been administered in combination.
Figure 3:
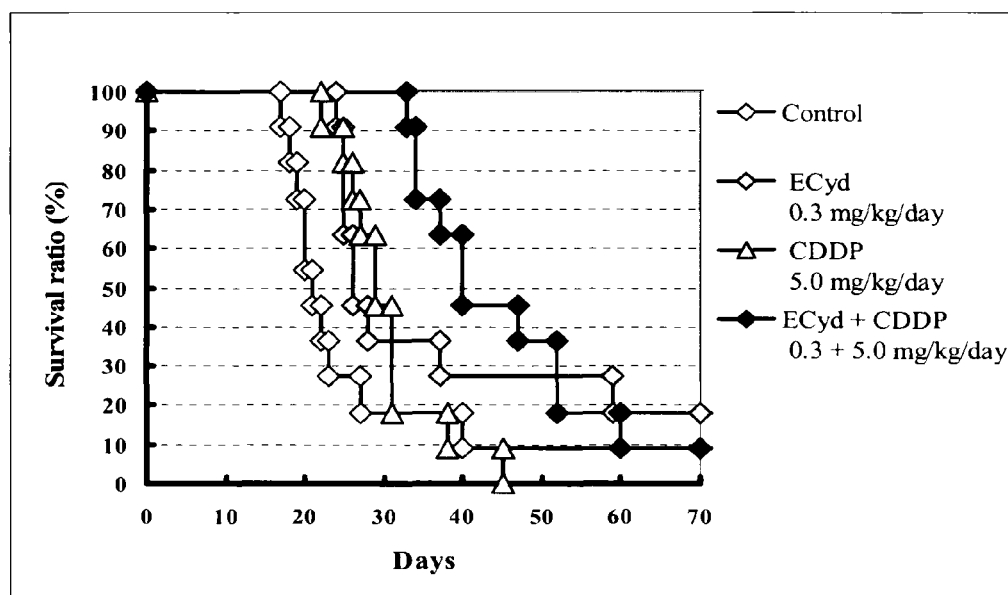
FIG. 3 A graph showing survival of subjects to which 0.3 mg/kg/day ECyd and 5 mg/kg/day cisplatin have been administered in combination.

Thereafter, the survival (days) of each rat was checked, and the survival rate of each group was calculated by the following equation 1. FIGS. 1 to 3 are graphs showing survival rates; in each graph the horizontal axis represents days and the vertical axis represents survival rate.

Survival rate (%)=(no. of surviving rats/no. of rats tested)×100    (Equation 1)

As is clear from FIGS. 1 to 3, the combined administration group (ECyd and carboplatin) exhibited statistically significant prolongation of survival, as compared with the ECyd-only administration group and the carboplatin-only administration group. Therefore, administration of ECyd and carboplatin in combination was found to provide a synergistic antitumor effect (FIGS. 1 and 2). Meanwhile, in the case of administration of ECyd and cisplatin in combination, the survival rate on day 70 was almost equivalent to that of the ECyd-only administration group. Therefore, the synergistic effect with cisplatin was very limited (FIG. 3).

On day 70, the combined administration group (ECyd and carboplatin) exhibited a survival rate as remarkably high as about 40 to 50%, while the survival rate of the combined administration group (ECyd and cisplatin) was about 10%, indicating that administration of ECyd and carboplatin in combination is a very useful therapeutic method. Note that potentiation of antitumor effect by administration of carboplatin and ECyd in combination is attained at a remarkably high degree, as compared with that by administration of cisplatin and ECyd in combination. Since cisplatin and carboplatin are similar to each other in terms of chemical structure (i.e., platinum complex) and action mechanism (i.e., DNA synthesis inhibition), the surprising results are unexpected by those skilled in the art.

Example 2

A fragment (about 2×2 mm) of human lung cancer strain LX-1 was subcutaneously transplanted in the back of each of male nude mice (BALB/cA jcl-nu). When the average tumor volume (longer diameter (mm)×shorter diameter (mm)×shorter diameter (mm)×½) of these mice reached about 200 mm$^3$, the mice were divided into groups based on the tumor volume (8 mice in each group) (day 0).

Drug administration was started on the day following transplant (day 1). ECyd and carboplatin were administered to a mouse through the caudal vein at a dose of 2 mg/kg and 70 mg/kg, respectively, on days 1 and 8. Mice of a control group were not subjected to drug treatment.

On day 15, the ratio of tumor volume to that at the grouping (Relative Tumor Volume; RTV) was calculated. In addition, percent inhibition of tumor proliferation of a group with respect to the control group (Inhibition Rate (%); IR (%)) was calculated by equation 2.

From the tumor volume on day 15, enhancement in antitumor effect of the combined administration group with respect to the ECyd-only administration group and the carboplatin-only administration group was analyzed through the Student's t-test (both sides). The antitumor effect of the combined administration group with respect to either single administration group had significance value (p value) of less than 0.05, confirming that administration of ECyd and carboplatin in combination is statistically significant. The results are shown in the following Table 1.

IR (%)=[1−average tumor volume of treated group/average tumor volume of control group]×100    (Equation 2)

TABLE 1

| Drug | Dose (mg/kg/day) | RTV Mean ± SD | IR (%) |
|---|---|---|---|
| Control | — | 9.67 ± 2.65 | — |
| ECyd | 2 | 5.43 ± 1.51 | 43.8 |
| carboplatin | 70 | 5.53 ± 1.75 | 42.8 |
| ECyd + carboplatin | 2 + 70 | 3.77 ± 0.73* | 61.0 |

*Enhancement in antitumor effect of the combined administration group with respect to the ECyd-only administration group and the carboplatin-only administration group was analyzed through the Student's t-test (both sides) (p < 0.05)

These experiments have revealed that a therapy employing ECyd and carboplatin in combination is effective for treating various cancers, such as head and neck cancer and lung cancer, while suppressing adverse effects.

The invention claimed is:

1. An antitumor agent containing 1-(3-C-ethynyl-β-D-ribopentofuranosyl)cytosine or a salt thereof, and carboplatin in combination.

2. The antitumor agent according to claim 1, which is a combined drug.

3. The antitumor agent according to claim 1, which is in the form of a kit including a drug containing 1-(3-C-ethynyl-β-D-ribopentofuranosyl)cytosine or a salt thereof and a drug containing carboplatin.

4. A method for treating cancer, comprising administering 1-(3-C-ethynyl-β-D-ribopentofuranosyl)cytosine or a salt thereof and carboplatin, to a patient in need thereof in combination.

5. The method for treating cancer according to claim 4, wherein 1-(3-C-ethynyl-β-D-ribopentofuranosyl)cytosine or a salt thereof and carboplatin are administered to a patient in need thereof simultaneously, or separately at an interval.

6. A method for potentiating antitumor effect of carboplatin, comprising administering 1-(3-C-ethynyl-β-D-ribopentofuranosyl)cytosine or a salt thereof to a patient to which carboplatin is administered, in effective amount for the antitumor effect of carboplatin being significantly potentiated.

7. The antitumor agent according to claim 1, wherein said agent comprises 0.1 to 100 mg of 1-(3-C-ethynyl-β-D-ribopentofuranosyl)cytosine or a salt thereof.

8. The antitumor agent according to claim 1, wherein said agent comprises 00.1 to 10 g of carboplatin.

9. The method according to claim 4, wherein the amount of 1-(3-C-ethynyl-β-D-ribopentofuranosyl)cytosine or a salt thereof administered to a patient in need thereof ranges from 0.01 to 200 mg/m$^2$/day.

10. The method according to claim 4, wherein the amount of 1-(3-C-ethynyl-β-D-ribopentofuranosyl)cytosine or a salt thereof administered to a patient in need thereof ranges from 0.05 to 100 mg/m$^2$/day.

11. The method according to claim 4, wherein the amount of carboplatin administered to said patient in need thereof ranges from 0.01 to 20 mg/m$^2$/day.

12. The method according to claim 4, wherein the amount of carboplatin administered to said patient in need thereof ranges from 0.01 to 10 mg/m$^2$/day.

\* \* \* \* \*

UNITED STATES PATENT AND TRADEMARK OFFICE
CERTIFICATE OF CORRECTION

PATENT NO.       : 8,586,561 B2
APPLICATION NO. : 12/934772
DATED            : November 19, 2013
INVENTOR(S)      : Hiromi Kazuno It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 378 days.

Signed and Sealed this
Twenty-second Day of September, 2015

Michelle K. Lee
*Director of the United States Patent and Trademark Office*